United States Patent [19]
O'Rourke et al.

[11] Patent Number: 5,774,610
[45] Date of Patent: Jun. 30, 1998

[54] FIBER OPTIC PROBE

[75] Inventors: Patrick E. O'Rourke, Martinez, Ga.; William R. Toole, Jr., Aiken, S.C.

[73] Assignee: Equitech Int'l Corporation, Aiken, S.C.

[21] Appl. No.: 676,432

[22] Filed: Jul. 8, 1996

[51] Int. Cl.$^6$ ..................................... G02B 6/26
[52] U.S. Cl. ........................................... 385/52
[58] Field of Search ................. 385/52, 12, 15, 385/39, 43, 123, 127, 128, 901; 250/227.11, 227.21, 227.14, 306, 311, 227.29, 227.28; 356/364, 336, 338; 340/604, 605, 619, 583, 600, 601

[56] References Cited

U.S. PATENT DOCUMENTS

| | | |
|---|---|---|
| 3,190,735 | 6/1965 | Kapany . |
| 3,198,059 | 8/1965 | Phaneuf et al. . |
| 3,224,851 | 12/1965 | Hicks, Jr. . |
| 3,301,648 | 1/1967 | Sheldon . |
| 3,586,562 | 6/1971 | Jones . |
| 3,681,164 | 8/1972 | Bazinet, Jr. et al. . |
| 4,173,392 | 11/1979 | Ekinaka et al. . |
| 4,573,761 | 3/1986 | McLachlan et al. . |
| 4,662,749 | 5/1987 | Hatton et al. ........................... 356/336 |
| 4,923,268 | 5/1990 | Xu . |
| 5,017,772 | 5/1991 | Hafle ................................. 250/227.28 |
| 5,030,000 | 7/1991 | Berkner ............................. 250/227.11 |
| 5,058,985 | 10/1991 | Davenport et al. . |
| 5,185,832 | 2/1993 | Coutandin et al. . |
| 5,222,180 | 6/1993 | Kuder et al. . |
| 5,259,056 | 11/1993 | Davenport et al. . |
| 5,304,172 | 4/1994 | Manoukian et al. ....................... 606/60 |
| 5,402,508 | 3/1995 | O'Rourke et al. ....................... 385/115 |
| 5,404,218 | 4/1995 | Nave et al. ............................. 356/301 |
| 5,410,151 | 4/1995 | Buckland ........................... 250/227.26 |
| 5,519,801 | 5/1996 | Le Noane et al. . |
| 5,661,843 | 8/1997 | Rickenbach et al. ................... 385/147 |
| 5,664,036 | 9/1997 | Islam ........................................ 385/31 |

OTHER PUBLICATIONS

S. E. Nave, et al., "Sampling Probes Enhance Remote Chemical Analyses," *Laser Focus World*, Dec., 1995, pub. PennWell Publishing Company, USA.

*Primary Examiner*—Akm E. Ullah
*Attorney, Agent, or Firm*—Maria Reichmanis

[57] ABSTRACT

A fiber optic probe and optical coupler assembly for light scattering measurements, and a method for making the assembly and aligning a plurality of optical fibers therein. The probe includes a probe body with a window across its tip for protecting the interior, at least one light-transmitting fiber, at least one light-receiving fiber, and (if desired), in-line devices such as filters and lenses positioned in optical communication with the fibers. A fiber optic coupler maintains the relative alignment of the fibers, which can be cut to install filters and other in-line devices. The coupler allows the cut ends to be re-aligned quickly and accurately without the need for time-consuming procedures or costly precision alignment equipment. The probe is simple, rugged, requires no high-precision machining or optical alignment procedures in assembly, and is economical to manufacture.

18 Claims, 4 Drawing Sheets

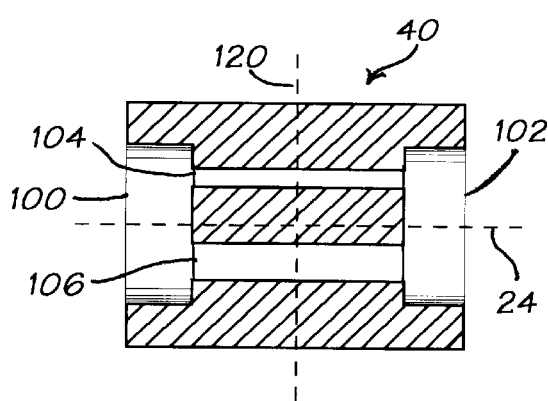
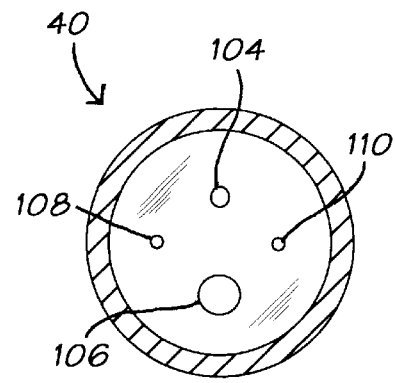
Fig. 4A
Fig. 4B
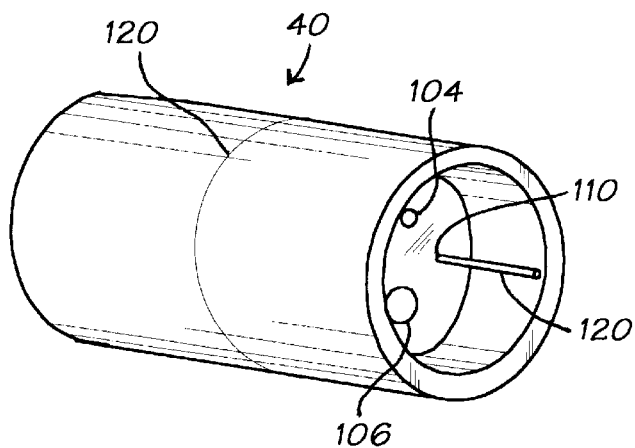
Fig. 4C
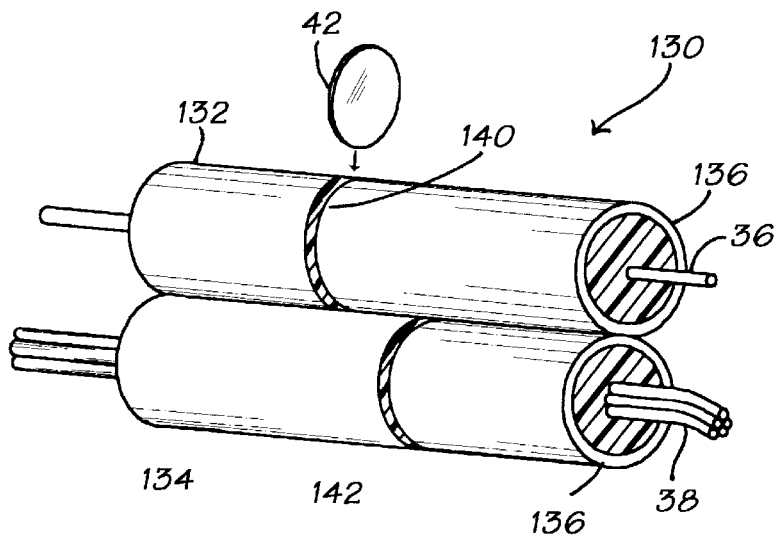
Fig. 5

FIBER OPTIC PROBE

BACKGROUND OF THE INVENTION

1. Field of the Invention

The present invention relates to fiber optic probes for spectrophotometry. In particular, the present invention relates to a rugged, mechanically stable fiber optic probe and optical coupler assembly for light scattering measurements, and to a method for making the probe.

2. Discussion of Background

Recent developments in fiber optics, coupled with the availability of multichannel array-type spectrometers and multiplexing technology, have generated renewed interest in the use of remote spectroscopic techniques for in-line monitoring and process control, environmental monitoring, and medical applications. Signal transmission via optical fibers allows the placement of sensitive equipment in locations remote from industrial process streams, making remote sensing particularly attractive in harsh environments. Multiplexing—the capability of transmitting signals from a plurality of sources to a single instrument—facilitates the efficient use of complex and expensive instrumentation. Optical analysis techniques also improve the quality of the data. Data obtained from a sample is not always truly representative of the source of that sample, since the mere act of taking the sample can alter its properties; frequently, removing a sample can perturb the source as well. Optical analysis techniques can usually be undertaken without removing samples for laboratory analysis elsewhere; therefore, data from optical analyses is frequently more reliable than data obtained by other analytical techniques.

Remote fiber optic probes are essential for in-line monitoring and process control in corrosive and radioactive process environments. In the environmental field, fiber optic probes are used for in situ measurements of fluids in wells, boreholes, storage and process tanks, and so forth. Applications include monitoring groundwater flow, studying the migration of subsurface contaminants, evaluating the progress of remediation operations, and detecting toxic or explosive substances. Fiber optic probes can be used with absorption, diffuse reflectance, and Raman spectroscopy.

The absorbance of a substance is defined as $A=-\log_{10}T$, where $T=I/I_0$, I is the transmitted light intensity, and $I_0$ the incident light intensity. The absorption spectrum of a substance—the frequency distribution of the absorbance—is used to identify its composition; the amount of light absorbed at different frequencies depends on the concentration of each constituent. Spectrophotometry is the measurement of this absorption spectrum. A typical spectrophotometer includes these basic components: a light source, a probe containing light-transmitting and light-receiving fibers, and a detector. Light from the source is directed to the substance of interest by the transmitting fiber. The light is transmitted through the substance to the receiving fiber and the detector, which produces an output signal proportional to the absorbance of the substance over a range of frequencies. Measurements taken from a suitable reference sample are compared to measurements taken from the test sample to help determine the concentrations of various constituents in the test sample.

Absorption spectroscopy requires samples that are optically translucent or transparent in the range of frequencies being studied. Other techniques based on analysis of the light scattered by the sample, such as diffuse reflectance, fluorescence, and Raman spectroscopy, are useful for in situ analysis of solids or slurries (as used herein, the term "scattered light" includes both elastic (Rayleigh) scattering and inelastic (Raman and fluorescence) scattering). In probes designed for these types of measurements, light is directed to the sample through a transmitting fiber; scattered light is collected by the receiving fiber and returned to the detector. Probes designed for Raman spectroscopy can also be used for fluorescence. For purposes of the following discussion, the terms "Raman spectroscopy" and "Raman measurements" include all forms of inelastic scattering phenomena.

Raman spectroscopy is a sensitive analytical technique based on the inelastic scattering of light (typically, monochromatic light from a laser) by an atom or molecule. While most of the scattered light has the same frequency as the incident light (Rayleigh scattering), a portion is frequency-shifted by an amount equal to one of the resonant frequencies of the molecule. Therefore, in addition to elastically-scattered light having the same frequency as the incident light, the scattered light contains small amounts of light with different frequencies. The pattern of frequency shifts is characteristic of the constituents of the sample; the intensity depends on the concentrations of each constituent in the sample. Raman spectroscopy provides an excellent indicator, or fingerprint, of the types of molecules present in a sample.

Vibrational and rotational Raman spectra are typically in the visible or near-infrared (NIR) region, therefore, Raman spectra are less severely attenuated than infrared (IR) absorption spectra by transmission over optical fibers. Therefore, Raman spectroscopy can be done with normal silica fiber optic cables instead of the more expensive and fragile types of fibers needed for IR absorption spectroscopy. In addition, Raman spectroscopy is particularly useful for identifying the constituents of a substance since Raman spectra generally contain more spectral lines—and sharper lines—than other types of spectra.

A problem encountered in Raman spectroscopy is the small scattering cross section, that is, the very low intensity of the Raman-scattered light compared to the intensity of the incident light (also termed the "exciting light"). Like absorption spectroscopy, Raman spectroscopy requires a light source, an optical probe with light-transmitting and light-receiving fibers (also termed exciting and collecting fibers, respectively), and a detector. In addition to Raman-scattered light, some of the exciting light and some elastically-scattered light are reflected back to the receiving fiber. Light may also be reflected to the receiving fiber by the interior surfaces of the probe. In addition, monochromatic light transmitted by an optical fiber excites the fiber molecules, causing fluorescence and Raman scattering within the fiber itself. This "self-scattering" or "silica scattering" generates a signal that interferes with the Raman signal collected from the sample of interest.

When making Raman measurements with fiber optics, it is therefore necessary to reduce the amounts of nonshifted sample-induced scattered and reflected light returning to the spectrometer, as well as reduce fluorescence and silica Raman scattering generated in the fibers themselves. To filter out this noise, light from the transmitting fiber may be directed through a narrow bandpass filter at the fiber tip that transmits the laser frequency but rejects signals arising from the fiber (fluorescence and silica scattering) and extraneous light from the laser source (such as plasma lines, fluorescence, or superluminance). Light returning through the receiving fibers passes through a long-pass optical filter that rejects elastically-scattered light and reflected laser light but transmits Raman signals from the sample. High-intensity laser sources and sensitive detectors with high light gathering power and high stray light rejection are needed to isolate and measure the low intensity Raman signal due to the sample. Chemometric techniques are also used to help factor out background noise and identify the signal of interest. Instrumentation for Raman spectroscopy is costly and delicate, requires high-precision, high-maintenance optical components, and is not well suited for use in many industrial process environments.

Presently-available fiber optic Raman probes include a probe having slanted tips (McLachlan, et al., U.S. Pat. No. 4,573,761). The transmitting fiber is surrounded by a plurality of receiving fibers spaced about the axis of a cylindrical housing which is closed at one end by a transparent window. The receiving fibers converge along lines which intersect at a point that is adjacent to or beyond the outer surface of the window. A Raman probe for light scattering measurements may include fibers with angled endfaces, such as the probe described in U.S. Pat. No. 5,402,508 issued to O'Rourke, et al., the disclosure of which is incorporated herein by reference. A variety of fiber optic probes, including Raman probes, are described by S. E. Nave, et al. in "Sampling probes enhance remote chemical analyses," *Laser Focus World*, December, 1995 (incorporated herein by reference). Several commercially available probes include efficient dual-fiber designs incorporating micro-optics, beamsplitters, and filters at the probe tip (such probes are available from Dilor Instruments SA (Edison, N.J.) and EIC Laboratories (Norwood, Mass.)).

A variety of closely packed multifiber arrays and processes for making such arrays are known in the art. Le Noane, et al. (U.S. Pat. No. 5,519,801) describe multicore optical guides wherein the optical fibers are very accurately positioned with respect to one another and with respect to the external contours of a matrix. Kuder, et al. (U.S. Pat. No. 5,222,180) place a bundle of polymer optical fibers into a rigid sleeve that has a softening point higher than the softening point of the fibers. When the resulting assembly is heated, the fibers expand, resulting in a close-packed geometry.

Ekinaka, et al. (U.S. Pat. No. 4,173,392) and Bazinet, Jr., et al. (U.S. Pat. No. 3,681,164) use bonding agents to hold a plurality of fibers in place. The Ekinaka, et al. glass fiber light guide consists of an elongated bundle of generally parallel glass fibers embedded in a hardened resin matrix, sheathed by a pair of thin protective layers. Bazinet, Jr., et al. apply a ceramic-based bonding agent to a bundle of fiber optic tips, then pull the bundle back into a plug until the tips are flush with the end.

Other methods for holding fibers in place include heat-shrinkable tubing and cords. Jones (U.S. Pat. No. 3,586, 562), Hicks, Jr. (U.S. Pat. No. 3,224,851), and Phaneuf, et al. (U.S. Pat. No. 3,198,059) use heat shrinkable plastic tubing to secure the ends of a fiber bundle in place. Sheldon ties a cord about the ends of a bundle, then dips the ends in a cohesive liquid agent to permanently fix the ends in position (U.S. Pat. No. 3,301,648). The resulting bundle can be covered by heat-shrink tubing. Kapany makes a multifiber bundle by aligning a plurality of glass rods within a tube, then draws the resulting structure to the desired diameter (U.S. Pat. No. 3,190,735).

Multifiber couplers are used in many fiber optic devices. In U.S. Pat. Nos. 5,289,056 and 5,058,985, Davenport, et al. disclose an optical coupler that includes a housing and a plurality of optical fibers, the output ends of which are distributed to various spaced-apart locations. The input ends of the fibers are stripped of cladding, then compressed together within an inner sleeve so that boundaries between the individual ends are substantially eliminated. To protect the input ends from damage by high brightness light sources, a light-transmissive rod with a higher thermal coefficient than the fibers is disposed in optical contact with the input ends. Coutandin, et al. and Xu also use heat-shrinkable tubing in their devices. Coutandin, et al. (U.S. Pat. No. 5,185,832) make an optical coupler by bundling a plurality of polymer optical waveguides inside a plastic tube, pushing a heat-shrinkable sleeve over the tube, and heating to a temperature at which the sleeve contracts. Xu (U.S. Pat. No. 4,923,268) uses fibers that have a heat fusing temperature in a range achievable by exterior heating of a shrink sleeve. In his device, the fibers are fused together along a limited length within the sleeve.

Presently-available Raman probes depend on precision optical components and single-strand optical fibers for excitation and light collection. Assembly of such probes requires high-precision machining and stringent optical alignment procedures. The probes are expensive and delicate, rendering them unsuitable for most field installations. In part because of these problems, in part because other needed instruments were large, complex, and expensive, Raman spectroscopy has historically been confined to research laboratories.

Despite the availability of numerous fiber optic probes, there is a need for a simple, rugged, inexpensive and easy-to-manufacture probe for light scattering measurements (including Raman spectroscopy). Such a probe would further the use of Raman spectroscopy for on-line monitoring in a wide range of laboratory, medical, environmental, and industrial environments.

SUMMARY OF THE INVENTION

According to its major aspects and broadly stated, the present invention is a fiber optic probe and optical coupler assembly, and a method for making the assembly and precisely aligning a plurality of optical fibers therein. The probe includes a probe body with a window across its tip for protecting the interior, at least one light-transmitting fiber and at least one light-receiving fiber, and (if desired), in-line devices such as filters and lenses positioned in optical communication with the fibers by a fiber optic coupler. The probe is simple, rugged, can be assembled without high-precision machining or optical alignment procedures, and is economical to manufacture.

In use, the probe is placed near a sample with the transmitting fiber in optical communication with a light source and the receiving fiber in optical communication with a spectrophotometer. Exciting light is directed to the sample by the transmitting fiber, where at least a portion of the light interacts with the sample to produce Raman-scattered light. Some of the scattered light is collected by the receiving fiber or fibers, and transmitted to a detector where the Raman spectrum of the sample is recorded and analyzed.

An important feature of the present invention is the fiber optic coupler, which maintains the relative axial alignment of the transmitting fiber and the receiving fiber. The fibers can be cut to install in-line devices such as filters, and the cut ends re-aligned quickly and essentially perfectly without the need for costly precision alignment equipment.

Another important feature of the present invention is the probe. The design of the probe allows exciting light to interact with a sample to produce Raman-scattered light, but largely prevents the exciting light from interfering with the low-intensity Raman signal. The probe is connected to a suitable light source (preferably, a laser) and a spectrophotometer by optical fibers, thereby facilitating remote monitoring in a wide range of environments.

Another feature of the present invention is the probe tip. A window is placed across the tip to protect the optical fibers and other interior components of the probe from the samples being measured (and, in some cases, from harsh industrial process environments). The fibers themselves may have slanted endfaces to maximize the collection of scattered light, thereby increasing the efficiency of the probe for low-intensity Raman measurements.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 4A is a detail, cross-sectional view of the fiber optic coupler of FIG. 1;

FIGS. 4B and 4C are end and perspective views, respectively, of the coupler of FIG. 4A;

FIG. 5 is a perspective view of another fiber optic coupler according to the present invention;

DETAILED DESCRIPTION OF A PREFERRED EMBODIMENT

Figure 1:
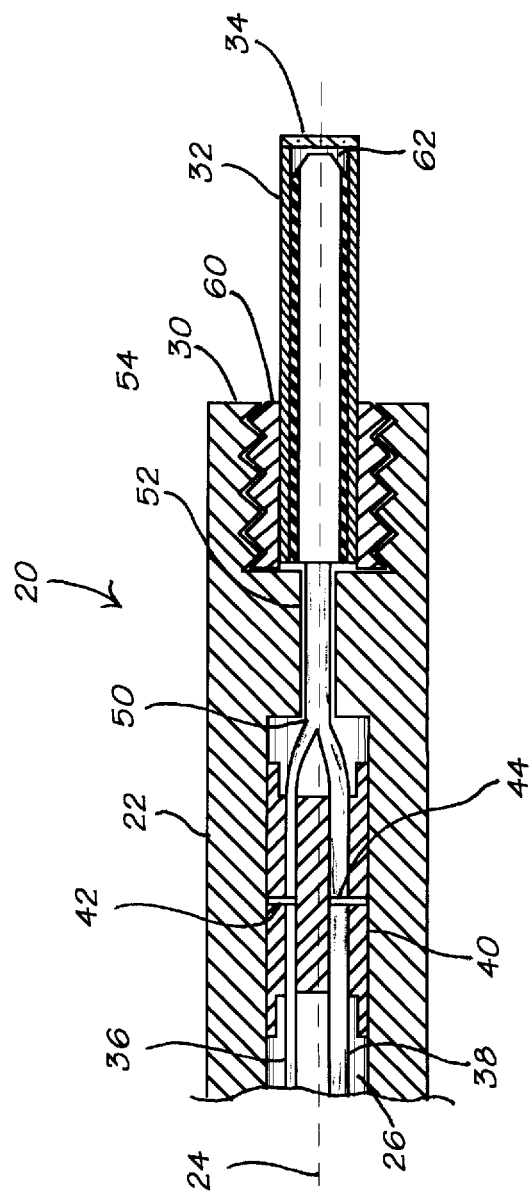
FIG. 1 is a cross-sectional view of a fiber optic probe according to a preferred embodiment of the present invention.

In the following description, reference numerals are used to identify structural elements, portions of elements, or surfaces in the drawings, as such elements, portions or surfaces may be further described or explained by the entire written specification. For consistency, whenever the same numeral is used in different drawings, it indicates the same element, portion, surface and area as when first used. As used herein, the terms "horizontal," "vertical," "left," "right," "up," "down," as well as adjectival and adverbial derivatives thereof, refer to the relative orientation of the illustrated structure as the particular drawing figure faces the reader.

Referring now to FIG. 1, there is shown a fiber optic probe 20 according to a preferred embodiment of the present invention. Probe 20 includes a probe body 22 with a longitudinal axis 24, an interior 26, a proximal end 28, and a probe tip 32 with a window 34. At least one light-transmitting fiber 36, at least one light-receiving fiber 38, and a fiber optic coupler 40 are disposed in interior 26. In-line devices 42, 44 (lenses or filters) are positioned in optical communication with fibers 36, 38, respectively, preferably inside coupler 40 as shown. Fibers 36, 38 are separate near distal end 28 and inside coupler 40; however, the fibers are joined into a single fiber bundle 50 inside probe tip 32. Bundle 50 holds fibers 36, 38 in a fixed arrangement, for example, a plurality of receiving fibers 38 surrounding a transmitting fiber 36. In use, transmitting fiber 36 is in optical communication with a light source such as a laser (not shown); receiving fiber 38 is in optical communication with a spectrophotometer (not shown).

Interior 26 of probe body 22 includes a narrow bore 52 and a distal portion 54, which may be threaded as shown in FIG. 1. If desired, springs (not shown) may be positioned in interior 25 about fibers 36, 38, at the proximal end of coupler 40 and between the distal end of coupler and bore 52. A fitting 60 is mounted at the proximal end of probe tip 32, threaded so that fitting 60 can be screwed into probe body 22. Alternatively, fitting 60 may be integrally formed with tip 32; if portion 54 is not threaded, tip 32 may be press-fitted into portion 54 and secured in position by any convenient means. Fitting 60, if present, is preferably of a type that maintains fiber bundle 50 in a fixed angular position relative to probe body 22. That is, bundle 50 does not rotate with respect to probe body 22 while fitting 60 is being screwed into or out of the body 22.

Probe body 22 and coupler 40 are preferably made of materials that are substantially impervious to the environment in which probe 20 is used, such as stainless steel. Other materials may also be useful, including brass, aluminum, and alloys such as Inconel. Window 34 is a thin window made of a transparent material such as sapphire, quartz, silica, polymers such as polystyrene, polycarbonate, Teflon™ AF, or other suitable material, and is attached across the distal end of tip 34 so that a spacing 62 exists between the window and the distal end of fiber bundle 50. Window 34 is attached to probe tip 32 and positioned so as to avoid direct reflection from transmitting fiber 36 to receiving fibers 38. When window 34 is made of sapphire, the window is brazed into a metallic or ceramic tube (not shown) that provides a hermetically-sealed cover to protect the interior of probe tip 32. Other methods for attaching window 34 to the body of probe 20 may also be useful, depending on the material of the window and the anticipated uses of the probe. Depending on the choice of material for window 34, the thickness of the window, and the intended application of probe 20, the window may be substantially flat as shown, or curved.

Fibers 36, 38 are preferably single filament optical fibers with a transparent core, such as a fused silica core, enclosed in a cladding having a lower refractive index than the core. If desired, the fibers may be shielded by opaque jackets. The diameters of fibers 36, 38 are selected to optimize the collection of scattered light by receiving fibers 38. Fibers having core diameters of 300–600 microns are suitable for a broad range of applications; however, diameters outside this range may also be useful. When probe 20 is to be used in a radioactive environment, fibers 36, 38 are selected for good radiation resistance.

Figure 2A:
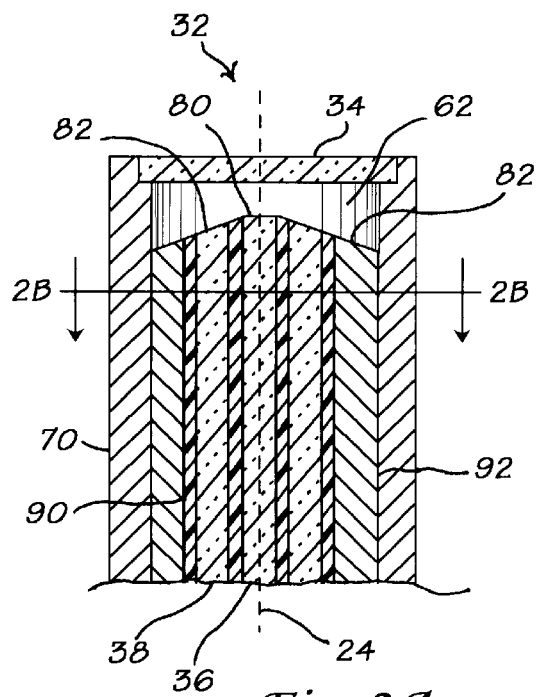
FIG. 2A is a detail view of the probe tip of FIG. 1.
Figure 2B:
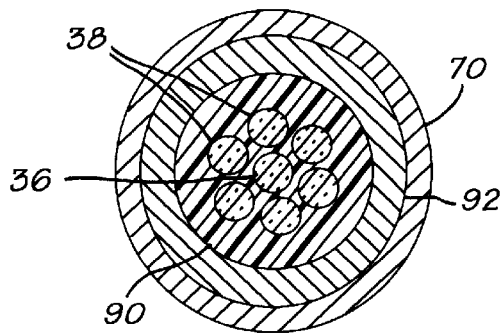
FIG. 2B is a cross-sectional view of the probe tip of FIG. 2A, taken along the lines 2B—2B of FIG. 2A.

Probe tip 32 is shown in detail in FIGS. 2A and 2B. Tip 32 includes a housing 70 with longitudinal axis 24, and contains at least one transmitting fiber 36 and at least one receiving fiber 38 (preferably, a plurality of receiving fibers 38 in a closely packed arrangement about the transmitting fiber). Fibers 36, 38 are oriented generally parallel to axis 24, thus, the fibers have optic axes parallel to axis 24. Transmitting fiber 36 has an endface 80 that is approximately perpendicular to axis 24 (and the optic axes of fibers 36, 38); receiving fibers 38 have endfaces 82 that are nonperpendicular to axis 24. As used herein, the term "endface" refers to the surface from which light enters or exits an optical fiber, that is, the surface at the cut end of the fiber. Endfaces 80, 92 may be shaped by cutting, grinding, polishing (to minimize imperfections on the cut surface) and like operations, preferably prior to attachment of tip 32 to probe body 22.

Fibers 36, 38 are held in position by a fixative 90 of epoxy or other suitable material. Fixative 90 is injected between fibers 36, 38 to maintain the spatial relationship and axial alignment of the fibers relative to housing 70 and each other. Probe tip 32 may also include a terminator 92. Fixative 90 adheres to the surfaces of fibers 36, 38, housing 70, and terminator 92 (if present) to hold the fibers securely within housing 70.

Figure 2C:
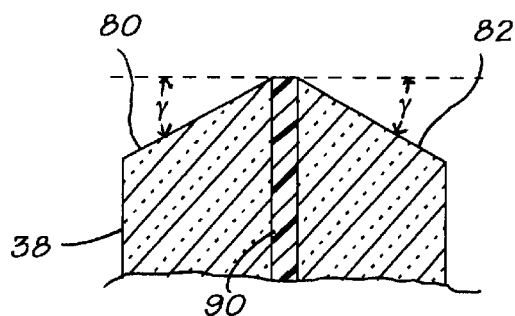
FIG. 2C is a detail view of the endfaces of two optical fibers of FIG. 2A, showing the bevel angle between the fibers.

Preferably, endfaces 80, 82 form a bevel having a bevel angle γ selected to minimize direct reflection of light from transmitting fiber 36 to receiving fiber 38 (FIG. 2C). Bevel angle γ is preferably less than approximately 20° (the effects of direct reflection are more apparent at angles greater than 20°). To further reduce crosstalk between transmitting and receiving fibers 36, 38, fixative 90 is preferably spiked with a light absorber such as carbon black.

The optimum thickness of window 34 and the optimum separation between endfaces 80, 82 and the inner surface of the window depend on the type of samples to be measured with probe 20. Typically, window 34 is closer to endfaces 80, 82 for probes 20 used with solid or gaseous samples; thicker windows may be needed for probes used with liquid samples.

When probe 20 is used for Raman measurements, laser light from a source (not shown) is transmitted by fiber 36 and directed through window 34 to the sample. The light strikes the sample molecules, causing at least a portion of the light to be scattered, and, to some extent, directed towards receiving fibers 38. The light received by fibers 38 (including Raman-scattered light and non-Raman-scattered light) is transmitted by the fibers to a spectrometer system, where the data are recorded and analyzed to determine the composition of the sample.

Because the endfaces of the receiving fibers (fibers 38) are angled with respect to the endface of transmitting fiber 36, their cones of acceptance/transmission are refractively bent inward and cross the light cone of the central (i.e., transmitting) fiber at a common point near the tip of probe 20. This effect results in enhanced signals in opaque slurries or solids by factors of five to ten when compared to probes having flat tips.

Figure 3A:
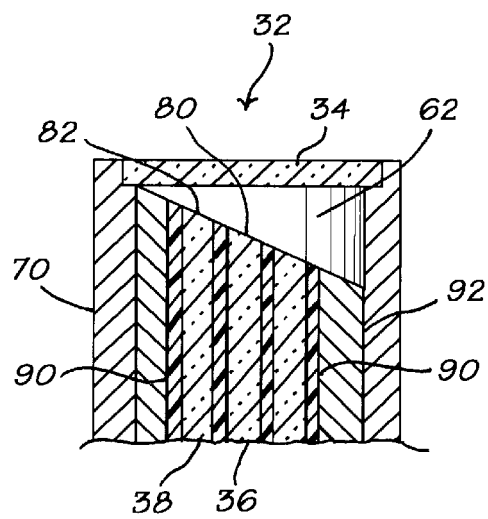
FIG. 3A is a detail, cross-sectional view of another probe tip usable with the invention.
Figure 3B:
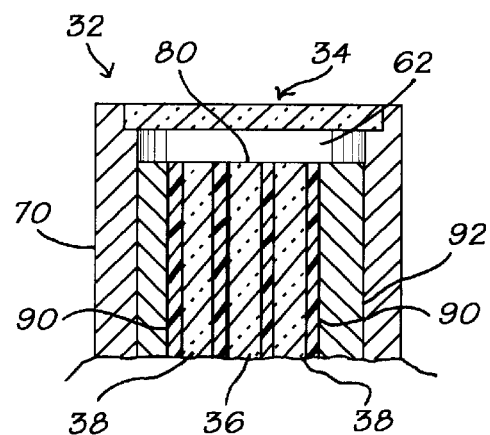
FIG. 3B is a detail, cross-sectional view of still another probe tip usable with the invention.

Other configurations of endfaces 80, 82 may also be useful in the practice of the invention. By way of example, endfaces 80, 82 may have a bevel angle of 0°, achieved by slanting the endfaces at the same angle (FIG. 3A), or cutting the endfaces substantially perpendicular to axis 24 (FIG. 3B).

Referring now to FIG. 4A, there is shown a cross-sectional view of fiber optic coupler 40. Coupler 40 has a first cavity 100 at its proximal end, a second cavity 102 at its distal end, and bores 104, 106 extending through the body of the coupler. Bores 104, 106 are dimensioned for holding optical fibers 36, 38, respectively. Depending on the particular application, coupler 40 may be made of brass, aluminum, stainless steel, or other metal or alloy.

Optical fibers 36, 38 are inserted into bores 104, 106 as shown in FIG. 1, and fixed in position by a suitable fixative (solder, epoxy, adhesive, and so forth). Each fiber is fixed over the entire length of its respective bore. If probe 20 is to include in-line devices 42, 44 (filters, lenses, and so forth), at least two alignment holes 108, 110 are drilled through the body of couples 40 (FIG. 4B). Then, coupler 40 is cut through a line 120 (FIGS. 4A, 4C), and the desired devices 42, 44 installed.

Devices 42, 44, if present, are any suitable optical devices that condition the light signal transmitted by fibers 36, 38, respectively. For example, device 42 may be a bandpass filter or laser pass filter that transmits the laser frequency but rejects other frequencies (including signals arising from transmitting fiber 36 (silica Raman and fluorescence) and extraneous light from the laser source (plasma lines, fluorescence, or superluminance)). Device 44 may be a laser rejection filter that rejects Rayleigh-scattered light and reflected laser light but transmits Raman signals from the sample.

Devices 42, 44 may be thin filters or lenses that are inserted in-line as shown in FIG. 5 (see below); alternatively, filter material may be deposited onto the cut surfaces of fibers 36, 38 by sputtering, painting, dipping, or other convenient technique.

After installation of devices 42, 44, the opposing cut ends of coupler 40 are brought together and re-aligned by inserting alignment pins such as pin 120 (FIG. 4C) into holes 108, 110. The cut ends are then fixed in position by any convenient technique. Alignment pins 120 may be removed if desired; alternatively, the pins may be left in place, fixed in position by epoxy, solder, or other suitable fixative.

Coupler 40 allows the easy installation of in-line filters and lenses without the need for time-consuming, high-precision optical alignment procedures. The original axial alignment of fibers 36, 38 with respect to each other is maintained simply by juxtaposing the cut ends of coupler 40 and adjusting the ends until pins 120 can be inserted through alignment holes 108, 110. The cut ends of each of fibers 36, 38 are then re-aligned essentially perfectly.

Figure 6:
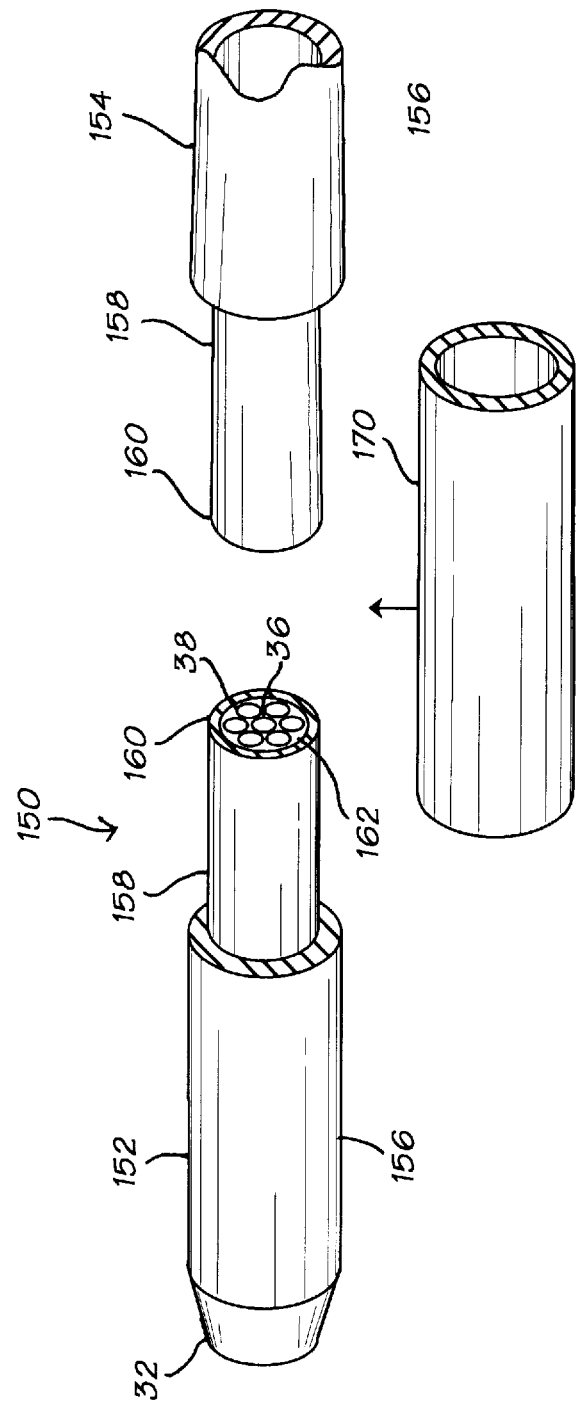
FIG. 6 is a perspective view of still another fiber optic coupler according to the invention.

Fiber optic couplers 130 and 150 according to additional preferred embodiments of the present invention are shown in FIGS. 5 and 6, respectively. Coupler 130 includes hollow tubes 132, 134 that contain fibers 36, 38, respectively (FIG. 5). Tubes 132, 134 may be joined together as shown by brazing, welding, soldering, or other convenient technique; fibers 36, 38 are fixed within their respective tubes by a suitable fixative (epoxy, solder, etc.). For insertion of a device 42, a slot 140 is cut into tube 132 (slot 140 is sufficiently deep to traverse fiber 36, and may extend through the entire thickness of tube 132). Device 42 is sandwiched into slot 40 and cemented in place. For insertion of a device 44 in-line with fiber or fibers 38, a similar slot 142 is cut into tube 134.

Slots 140 and 142 are preferably offset as shown in FIG. 5, thereby ensuring that the body of each tube 132, 134 will maintain the cut ends of the other tube in their relative positions with respect to each other. This ensures that the axial alignment of fibers 36, 38 is preserved—the fibers will still be aligned after insertion of in-line devices 42, 44. However, slots 140, 142 need not be offset if the slots extend only partway through the tubes. Preferably, slots 140, 142 are just wide enough for insertion of devices 42, 44, respectively.

Coupler 150 (FIG. 6) includes two portions 152, 154, each having an outer housing 156 and a tube 158 with a cut end 160 and a bore 162. Portion 152 may terminate in a probe tip such as above-described tip 32; portion 154 may be optically connected to a light source, a detector, and other instrumentation. The cut ends of transmitting fiber 36 and receiving fibers 38 are aligned with end 160 of portion 152 by butting tube 158 (with fibers 36, 38 inserted therein in any desired arrangement) against a flat surface. Fibers 36, 38 are then fixed inside tube 158 by epoxy or some other suitable fixative. Ends of matching fibers 36, 38 are similarly aligned inside tube 158 of portion 154. If desired, coupler 150 may be made in a single unit, then cut to form two portions 152, 154.

Devices 42, 44 are attached to some or all of fibers 36, 38, and portions 152, 154 connected to each other by means of a sleeve 170. Devices 42, 44 may be thin filters or lenses (such as device 42 shown in FIG. 5); alternatively, a suitable filter material may be deposited onto the surfaces of fibers 36, 38.

To assemble coupler 150, sleeve 170 is slipped over one of ends 160, then, the other end is inserted into the sleeve. When the two ends 160 are juxtaposed, their respective fibers 36 are aligned. Fibers 38 may be aligned by shining light down any one of fibers 38 of either of portions 152, 154, and rotating one of the portions to determine the angular position at which the transmitted light is maximized. At this position, all of fibers 36, 38 are correctly aligned.

Figure 7:
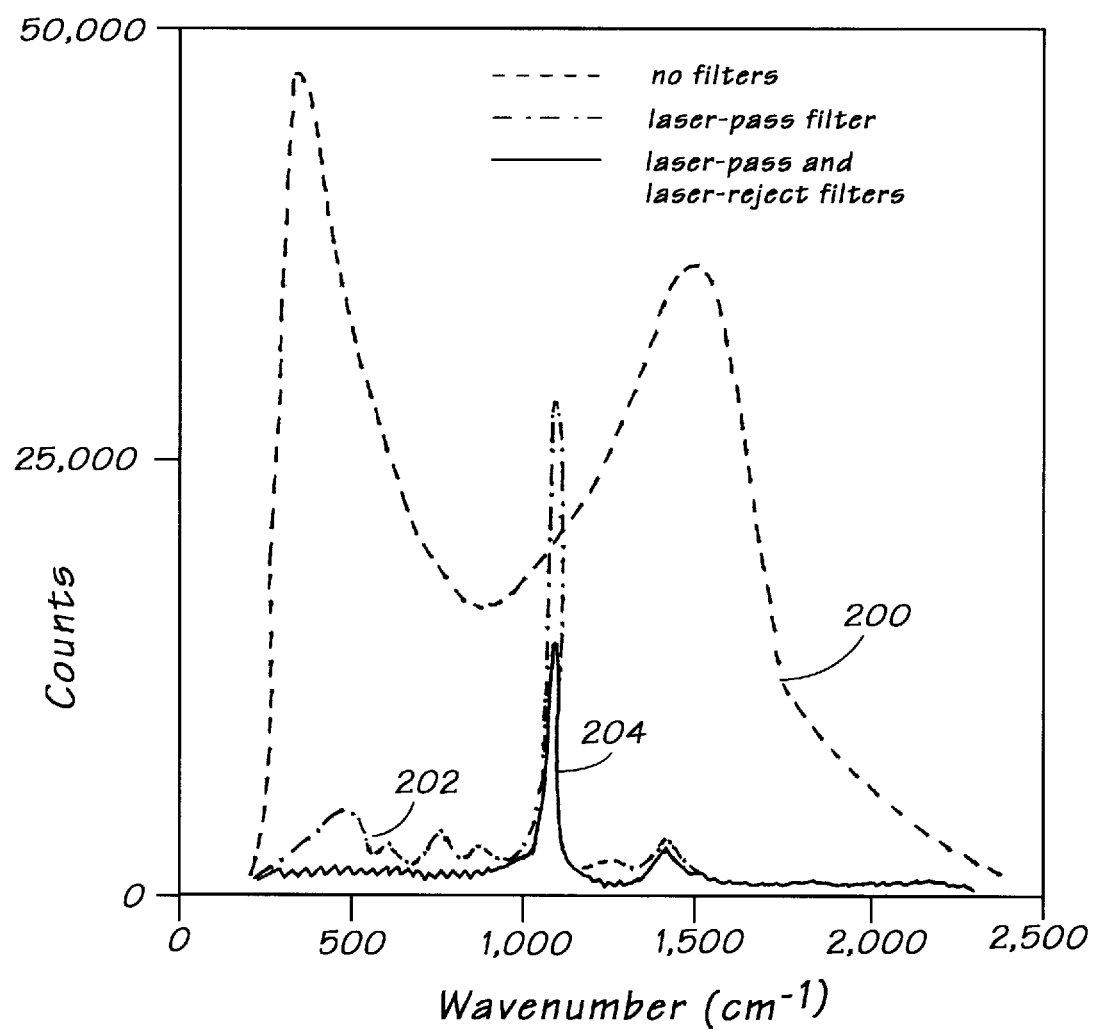
FIG. 7 shows the Raman spectrum of sodium nitrate.

An example of the type of data enhancement that is achievable with a proper choice of in-line filters (i.e., devices 42, 44) is shown in FIG. 7. The Raman spectrum of sodium nitrate powder was obtained without filters (spectrum 200), with a laser pass filter only (spectrum 202), and with laser-pass and laser-reject filters (spectrum 204). In-line filters produced sharper spectra; the greatest improvement was with both pass and reject filters (204).

Probe 20 is simple, rugged, and has a minimum of components. The probe is also economical to manufacture, and requires no high-precision machining or optical alignment procedures. Couplers 40, 130, 150 allow installation of devices such as in-line filters without optical connectors—the devices are simply placed where needed, and easily removed or replaced during routine servicing or to accommodate changed conditions. The particular components of probe 20 depend on the types of samples to be measured and the anticipated environment of use.

It will be apparent to those skilled in the art that many changes and substitutions can be made to the preferred embodiment herein described without departing from the spirit and scope of the present invention as defined by the appended claims.

What is claimed is:

1. A fiber optic probe for use in light scattering measurements, said probe comprising:
    a probe body having an interior and a longitudinal axis;
    at least one light-transmitting fiber in said interior, said transmitting fiber having a first optic axis;
    at least one light-receiving fiber in said interior, said receiving fiber having a second optic axis; and
    coupling means in said interior for holding said transmitting and receiving fibers in a fixed position with respect to each other within said coupler, said coupling means including means for aligning said transmitting and receiving fibers so that, when at least one fiber of said fibers in said coupling means is cut into two portions, each portion having a optic axis, said coupling means furthers alignment of said portions so that said optic axes of said portions approximately coincide.

2. The probe as recited in claim 1, wherein said first optic axis and said second optic axis are approximately parallel within said coupling means.

3. The probe as recited in claim 1, wherein said probe has a proximal end and a distal end, and wherein said first optic axis and said second optic axis are approximately parallel at said distal end.

4. The probe as recited in claim 1, wherein said probe has a proximal end and a distal end, further comprising means for holding said transmitting and receiving fibers in optical communication at said distal end so that, when a sample is positioned within a range beyond said distal end, at least a portion of light transmitted by said transmitting fiber is scattered by said sample, and at least a portion of said scattered light is collected by said receiving fiber.

5. The probe as recited in claim 1, wherein said at least one transmitting fiber has a first endface, said first endface being nonperpendicular to said first optic axis.

6. The probe as recited in claim 1, wherein said at least one transmitting fiber has a first endface, said first endface being approximately perpendicular to said first optic axis.

7. The probe as recited in claim 1, wherein said at least one receiving fiber has a second endface, said second endface being nonperpendicular to said second optic axis.

8. The probe as recited in claim 1, wherein said at least one receiving fiber has a second endface, said second endface being approximately perpendicular to said second optic axis.

9. The probe as recited in claim 1, further comprising a filter in optical communication with said transmitting fiber, said filter positioned inside said coupler and in-line with said transmitting fiber.

10. The probe as recited in claim 1, further comprising a filter in optical communication with said receiving fiber, said filter positioned inside said coupler and in-line with said receiving fiber.

11. A method for making a fiber optic probe for use in light scattering measurements, said method comprising the steps of:
    fixing at least one light-transmitting fiber in a coupler, said coupler having a longitudinal axis so that said transmitting fiber is approximately parallel to said longitudinal axis;
    fixing at least one light-receiving fiber in said coupler so that said transmitting fiber is approximately parallel to said longitudinal axis;
    forming a slot in said coupler, said slot passing through at least one of said transmitting and receiving fibers;
    installing a filter in said slot so that said filter engages a cut end of said at least one fiber; and
    installing said coupler with said light-transmitting fiber, said light-receiving fiber, and said filter in a housing.

12. The method as recited in claim 11, wherein said housing has a proximal end and a distal end, further comprising the step of axially orienting said transmitting and receiving fibers so that, when a sample is positioned within a range beyond said distal end, at least a portion of light transmitted by said transmitting fiber from a source is scattered by said sample, and at least a portion of said scattered light is collected by said receiving fiber.

13. The method as recited in claim 11, wherein said housing has a proximal end and a distal end, further comprising the step of attaching a window to said distal end to enclose said transmitting and receiving fibers within said probe, said window positioned just beyond said transmitting and receiving fibers.

14. The method as recited in claim 11, wherein said filter-installing step further comprises depositing a filter on said at least one cut end.

15. The method as recited in claim 11, wherein said transmitting fiber has a first optic axis, further comprising the step of forming a first endface on said transmitting fiber, said first endface being nonperpendicular to said first optic axis.

16. The method as recited in claim 11, wherein said receiving fiber has a second optic axis, further comprising the step of forming a second endface on said receiving fiber, said second endface being nonperpendicular to said second optic axis.

17. The method as recited in claim 11, wherein said transmitting and receiving fibers are fixed in said coupler with epoxy or solder.

18. The method as recited in claim 11, wherein said probe has a distal end, and wherein said transmitting and receiving fibers are fixed in said distal end with epoxy, said epoxy containing a light absorber to minimize crosstalk between said transmitting and receiving fibers.

\* \* \* \* \*